United States Patent
Humbert et al.

(10) Patent No.: US 8,992,613 B2
(45) Date of Patent: Mar. 31, 2015

(54) UNSHRUNKEN TISSUE EQUIVALENT AND METHODS FOR PRODUCING SUCH AN UNSHRUNKEN TISSUE EQUIVALENT

(75) Inventors: Philippe Humbert, Ornans (FR); Delphine Binda, Auxon Dessous (FR); Celine Viennet-Steiner, Ornans (FR); Sophie Robin, Pirey (FR); Helene Tauzin, Besancon (FR); Gwenael Rolin, Besancon (FR); Lionel Pazart, Besancon (FR)

(73) Assignees: Universite de Franche-Comte, Besancon (FR); Centre Hospitalier Universitaire de Besancon, Besancon (FR)

( * ) Notice: Subject to any disclaimer, the term of this patent is extended or adjusted under 35 U.S.C. 154(b) by 419 days.

(21) Appl. No.: 13/382,068

(22) PCT Filed: Jul. 1, 2010

(86) PCT No.: PCT/FR2010/051381
§ 371 (c)(1),
(2), (4) Date: Feb. 7, 2012

(87) PCT Pub. No.: WO2011/001116
PCT Pub. Date: Jan. 6, 2011

(65) Prior Publication Data
US 2012/0135520 A1 May 31, 2012

(30) Foreign Application Priority Data

Jul. 1, 2009 (FR) ...................................... 09 03215
Dec. 14, 2009 (FR) ...................................... 09 58919

(51) Int. Cl.
A61L 27/60 (2006.01)
A61F 2/10 (2006.01)
(Continued)

(52) U.S. Cl.
CPC ........... *C12N 5/0698* (2013.01); *A61L 27/3633* (2013.01); *A61L 27/3695* (2013.01);
(Continued)

(58) Field of Classification Search
None
See application file for complete search history.

(56) References Cited

U.S. PATENT DOCUMENTS 4,963,489 A * 10/1990 Naughton et al. ............. 435/1.1
6,699,287 B2 * 3/2004 Son et al. ................... 623/15.12
(Continued)

FOREIGN PATENT DOCUMENTS

WO      02083160 A2    10/2002
WO   2007052980 A1     5/2007

OTHER PUBLICATIONS

Gentilhomme et al: "Culture of dermal equivalent submitted to tension" Travaux Scientifiques des Chercheurs du Service de Sante des Armees, vol. 0, No. 15, 1994, pp. 149-150, XP009128409 ISSN: 0243-7473—English abstract.
Chapuis et al: "A new technique to study the mechanical properties of collagen lattices" Journal of Biomechanics, Pergamon Press, New York, NY, US, vol. 25, No. 1, Jan. 1, 1992, pp. 115-117,119, XP022873208 ISSN: 0021-9290 [extrait le Jan. 1, 1992].
Lafrance et al: "Mechanical properties of human skin equivalents submitted to cyclic tensile forces" Skin Research and Technology 199811 DK, vol. 4, No. 4, Nov. 1998, pp. 228-236, XP009128407 ISSN: 0909-752X.
(Continued)

*Primary Examiner* — Allison Fox
(74) *Attorney, Agent, or Firm* — Laurence A. Greenberg; Werner H. Stemer; Ralph E. Locher

(57) ABSTRACT

The invention relates to a method for producing an unshrunken tissue equivalent. Said method is comprising in that: a mixture is produced that contains at least one element of an extracellular matrix; at least one pluridimensional medium is soaked with said mixture; from the components of the mixture, a lattice comprising at least one element of an extracellular matrix is produced, at least at the medium; at least part of the components of said mixture is attached to the structure of the medium; the shrinking of at least the lattice is prevented and at least said lattice is tensioned on said medium; fibroblasts are integrated into the lattice and at least one cell culture of said fibroblasts is carried out, at least in the lattice. The invention also relates to a method for producing a skin equivalent that comprises at least one dermal equivalent formed by an unshrunken tissue equivalent and at least one epidermal equivalent.

7 Claims, 2 Drawing Sheets

(51) Int. Cl.
  *A61K 35/12* (2006.01)
  *C12N 5/071* (2010.01)
  *A61L 27/36* (2006.01)
  *A61L 27/38* (2006.01)

(52) U.S. Cl.
  CPC ............. *A61L27/3804* (2013.01); *A61L 27/60* (2013.01); *C12N 2502/094* (2013.01); *C12N 2502/1323* (2013.01); *C12N 2535/10* (2013.01)
  USPC ........ 623/15.12; 424/484; 424/422; 424/93.7

(56) References Cited

U.S. PATENT DOCUMENTS

| | | |
|---|---|---|
| 7,582,725 B2 | 9/2009 | Freyberg et al. |
| 2005/0079604 A1 | 4/2005 | Germain et al. |
| 2009/0209020 A1 | 8/2009 | Park et al. |
| 2010/0111931 A1 | 5/2010 | Freyberg et al. |

OTHER PUBLICATIONS

Khademhosseini et al: "Microscale technologies for tissue engineering and biology" Proceedings of the National Academy of Sciences of the United States of America Feb. 21, 2006 US, vol. 103, No. 8, Feb. 2006 (Feb. 21, 2006), pp. 2480-2487, XP002564980 ISSN: 0027-8424.

Petrulyte Salvinija: "Advanced textile materials and biopolymers in wound management." Danish Medical Bulletin Feb. 2008 LNKD—Pubmed:18321446, vol. 55, No. 1, Feb. 2008, pp. 72-77, XP009138164 ISSN: 1603-9629.

Rolin et al: "Assessment of tensile strength beneficial effects in an in vitro model of cutaneous wound healing" Journal of Investigative Dermatology, vol. 129, No. Suppl. 2, Sep. 2009, p. S81, XP009128388 & 39th Annual Meeting of the European-Society-For-Dermatological-Research; Budapest, Hungary; Sep. 9-12, 2009 ISSN: 0022-202X.

\* cited by examiner

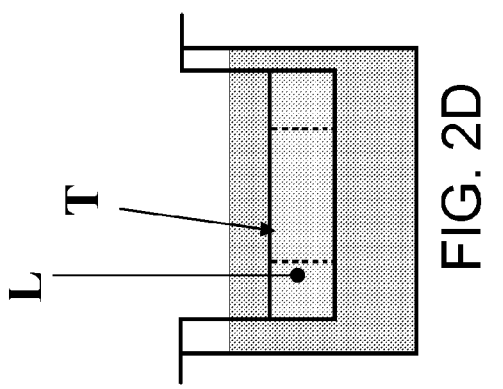
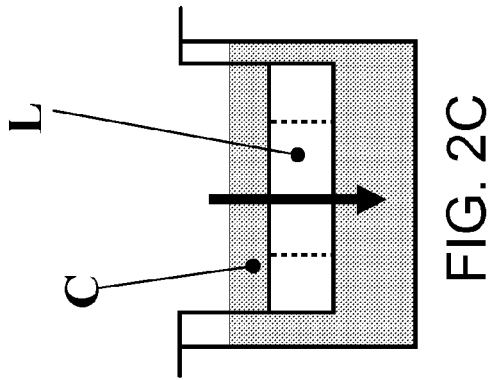
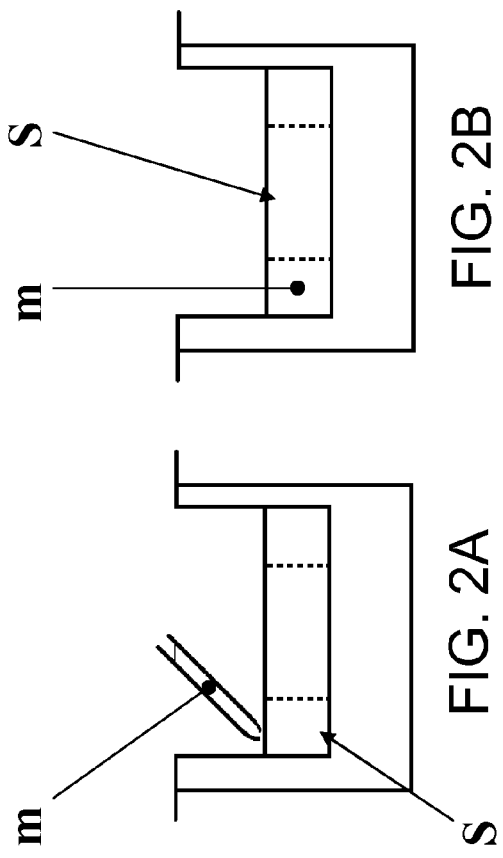

UNSHRUNKEN TISSUE EQUIVALENT AND METHODS FOR PRODUCING SUCH AN UNSHRUNKEN TISSUE EQUIVALENT

BACKGROUND OF THE INVENTION

Field of the Invention

The present invention relates to a method for producing an unshrunken tissue equivalent and also to a method for producing a skin equivalent comprising, on the one hand, at least one dermal equivalent made up of such an unshrunken tissue equivalent and, on the other hand, at least one epidermal equivalent.

This invention also relates to an unshrunken tissue equivalent, more particularly made up of a dermal equivalent, and also to a skin equivalent, in particular obtained by the respective implementation of these methods.

Thus, the present invention relates to the field of the production of the equivalent of at least one tissue, more particularly made up of a dermal equivalent, which is more particularly part of the composition of a skin equivalent, in particular a human skin equivalent.

Methods for producing such a skin equivalent, and which consist in taking a skin sample (usually by biopsy) from a donor, in placing this sample in culture under suitable conditions, and in grafting the skin equivalent obtained by means of this culture, are already known.

However, such a method has a certain number of drawbacks.

In particular, within a short space of time after the sample has been taken (in particular immediately after the biopsy) and/or during the culture period, the skin sample taken or the skin equivalent has a tendency to shrink.

This shrinking is accompanied, for the skin equivalent, by a modification of the initial functional characteristics exhibited by the cells of the skin to be sampled.

Finally, the shrinking of the grafted skin equivalent is accompanied by a particularly unattractive modification of the surface of the skin, at the level of the graft, or even at the periphery thereof.

BRIEF SUMMARY OF THE INVENTION

The present invention is meant to be able to remedy the drawbacks of the prior art methods for culturing dermis and skin.

To this effect, the invention relates to a method for producing an unshrunken tissue equivalent, in particular a human unshrunken tissue equivalent. This method is characterized in that it consists of the following:
  a mixture is produced that contains at least one element which is part of the composition of an extracellular matrix;
  at least one support, which is at least partly made up of a pluridimensional structure comprising cavities in the form of interstices and/or alveoli, made of a biocompatible material, and at least partly made up of a woven and/or knitted textile material, is soaked with at least one part of this mixture;
  from the components of this mixture, a lattice comprising at least one element which is part of the composition of an extracellular matrix is produced, at least at the support;
  at least one element of an extracellular matrix that the lattice comprises is attached to the structure of the support, by carrying out bioadhesion, to this structure, of at least one such element;
  the shrinking of at least the lattice is prevented and at least this lattice is kept under tension on this support;
  fibroblasts are integrated into the lattice and at least one cell culture of these fibroblasts is carried out, at least in the lattice, in order to obtain the unshrunken tissue equivalent.

An additional characteristic is that a support made of a textile material, extending in at least one plane, and exhibiting meshing, delimiting the cavities, and produced by weaving and/or knitting of fibers, is soaked with at least one part of the mixture.

More particularly, a support made of a textile material comprising at least two textile sheets, each extending in a plane parallel to the plane of another textile sheet, positioned at a predetermined distance from one another, so as to define between them an interstice constituting a cavity, comprising meshes delimiting cavities, positioned such that the meshes of two sheets are out of line, and connected to one another via filaments for preventing geometric deformation, is soaked with at least one part of the mixture.

The invention also relates to a method for producing a skin equivalent, in particular human skin equivalent, comprising at least one dermal equivalent and also at least one epidermal equivalent. This method is characterized in that it consists of the following:
  an unshrunken tissue equivalent made up of a skin dermal equivalent is produced by carrying out the method described above;
  the epidermal equivalent is then produced at the surface of the dermal equivalent obtained, by developing or by providing at least one layer of keratinocytes, before carrying out at least one cell culture of these keratinocytes.

This invention also relates to an unshrunken tissue equivalent, in particular human unshrunken tissue equivalent, more particularly obtained by carrying out the method described above. This unshrunken tissue equivalent is characterized in that it comprises:
  a support, which is at least partly made of a pluridimensional structure comprising cavities in the form of interstices and/or alveoli, made of a biocompatible material, and at least partly made up of a woven and/or knitted textile material;
  a lattice, which firstly comprises at least one element which is part of the composition of an extracellular matrix, which secondly is attached via bioadhesion to the structure of the support and kept under tension on this support, and which thirdly integrates at least fibroblasts and/or myofibroblasts resulting from cell differentiation of such fibroblasts.

Furthermore, the support, made of a textile material, extends in at least one plane, and exhibits meshing, delimiting the cavities, and produced by weaving and/or knitting of fibers.

In addition, the support, made of a textile material, comprises at least two textile sheets, each extending in a plane parallel to the plane of another textile sheet, positioned at a predetermined distance from one another so as to define between them an interstice constituting a cavity, comprising meshes delimiting cavities, positioned such that the meshes of two sheets are out of line, and connected to one another via filaments for preventing geometric deformation.

Finally, the invention relates to a skin equivalent, in particular a human skin equivalent, comprising at least one skin dermal equivalent and also at least one epidermal equivalent. This skin equivalent is in particular obtained by carrying out the method described above, and is characterized in that:

the skin dermal equivalent is made up of an unshrunken tissue equivalent as mentioned above;

the epidermal equivalent comprises at least one layer of keratinocytes.

In accordance with the present invention, the method for producing an unshrunken tissue equivalent consists, in particular, in attaching, to the structure of the support, at least one element, which is part of the composition of an extracellular matrix, and which is contained in a lattice integrating fibroblasts, before carrying out at least one cell culture of these fibroblasts.

Furthermore, the method for producing a skin equivalent, consisting in first of all producing an unshrunken tissue equivalent (made up of a dermal equivalent for this skin) by carrying out the abovementioned method, is also carried out while the lattice of the skin dermal equivalent is attached to the structure of the support.

Such an attachment makes it possible, advantageously and despite the natural tendency toward shrinking, to prevent this shrinking and to keep under tension, as appropriate, the tissue equivalent (more particularly, the dermal equivalent) and/or the skin equivalent.

By preventing such shrinking, firstly, the esthetic qualities of the skin equivalent are improved, secondly, functionalization of the cells is permitted (in particular differentiation of fibroblasts into myofibroblasts is permitted) and, thirdly, the functional characteristics of the cells are improved.

The abovementioned methods consist in producing, as appropriate, an unshrunken tissue equivalent (more particularly a skin dermal equivalent) and/or a skin equivalent comprising such a dermal equivalent.

Such an equivalent (tissue, dermal and/or skin) can be produced for research purposes, in particular pharmaceutical and/or pharmacological and/or toxicological research purposes, but also for therapeutic purposes, more particularly in the context of the temporary replacement of the barrier function in chronic pathological conditions with loss of cutaneous substance (for example leg ulcers), but also in the context of burns, bedsores, wounds after radiotherapy, or the like.

In the latter case and according to the clinical application envisioned, it is possible to provide either a dermal equivalent, or a replacement skin made up of a skin equivalent (comprising a dermal equivalent and also an epidermal equivalent), in order to ensure, by grafting, filling of a part devoid of cutaneous substance.

It will be observed that such grafting is here again carried out while keeping the dermal equivalent and the skin equivalent under tension and preventing shrinking thereof. This makes it possible, advantageously, to restore the skin functions and to provide the growth factors necessary for healing, at the graft.

Finally, keeping under tension and preventing shrinking makes it possible, advantageously, to substantially increase the surface area of unshrunken tissue equivalent produced, more particularly of dermal equivalent, and of skin equivalent obtained by carrying out the method according to the invention, compared with the surface area of skin sampled, in particular by biopsy.

Yet another advantage is that the method in accordance with the invention makes it possible to produce a dermal equivalent and a skin equivalent that are intended to be grafted onto the donor from whom the fibroblasts (or even the keratinocytes) having enabled the production of such an equivalent were taken, said production therefore being advantageously carried out autologously and eliminating any risk of graft rejection.

Furthermore and given that cells have different properties depending on their origin (arm, leg, etc.), the method in accordance with the invention advantageously makes it possible to confer on the cells of the graft the same properties as those of the cells of the sample taken.

An additional characteristic is that the method makes it possible to produce a skin equivalent capable of being grafted directly, immediately and in a single step, contrary to other skin substitutes of the prior art.

Finally, the method consists in carrying out an in vitro cell culture of fibroblasts, a sample of which can be advantageously taken by biopsy and the number of which is substantially smaller than that of the pinch grafts known in the prior art.

Other objectives and advantages of the present invention will emerge during the following description relating to embodiments which are given only by way of illustrative and nonlimiting examples.

Understanding of this description will be facilitated by referring to the appended drawings in which:

BRIEF DESCRIPTION OF THE SEVERAL VIEWS OF THE DRAWING

FIGS. 2a, 2b, 2c and 2d are diagrammatic views representing the various steps of the production of an unshrunken tissue equivalent;

FIGS. 3a, 3b, 3c, and 3d are diagrammatic views representing various steps of the production of a skin equivalent.

DESCRIPTION OF THE INVENTION

Figure 1:
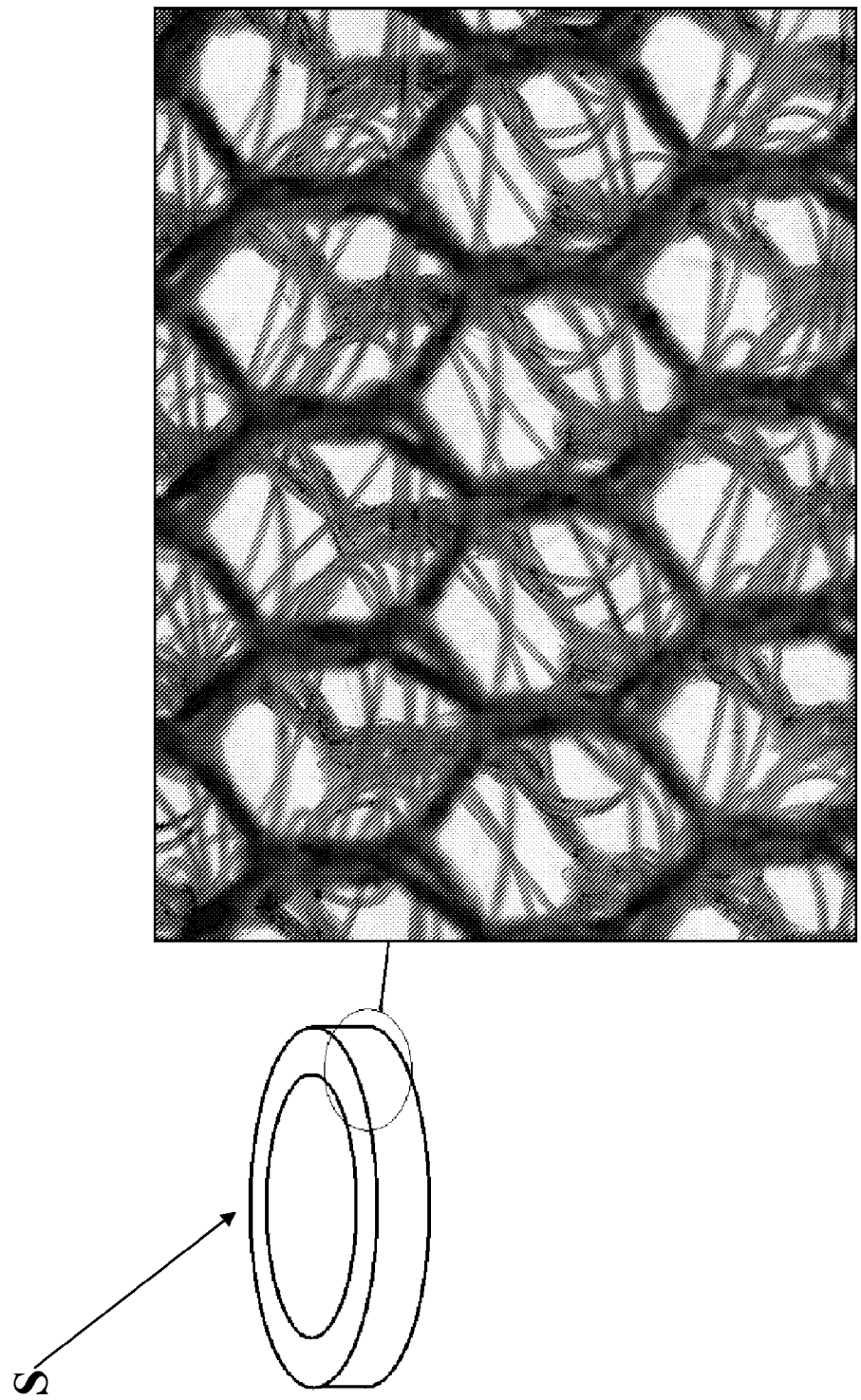
FIG. 1 is a diagrammatic view of a support intended to be soaked with a mixture containing at least one element which is part of the composition of an extracellular matrix and at least fibroblasts.

The present invention relates to the field of the production of the equivalent of at least one unshrunken tissue, in particular human tissue, and also of the equivalent of an organ comprising such an unshrunken tissue equivalent.

In this respect, it should be observed that such an unshrunken tissue equivalent T can be made up (in a nonlimiting manner) of:

a mucosal equivalent;

a membrane equivalent, in particular amniotic membrane equivalent;

a chorion equivalent;

an integument equivalent, more particularly a skin dermal equivalent, in particular human skin dermal equivalent.

The present invention therefore relates to, in the context of the production of an unshrunken tissue equivalent T, firstly, a method for producing such an unshrunken tissue equivalent T, in particular human unshrunken tissue equivalent T, and, secondly, an unshrunken tissue equivalent T obtained by carrying out this method.

In the particular case of an unshrunken tissue equivalent T made up of a skin dermal equivalent D, in particular human skin dermal equivalent D, the present invention relates to:

a method for producing an unshrunken tissue equivalent T made up of a dermal equivalent D and also such an unshrunken tissue equivalent T (made up of a dermal equivalent D) obtained by carrying out this method;

a method for producing a skin equivalent P (comprising at least one epidermal equivalent E and also at least one unshrunken tissue equivalent T made up of a dermal equivalent D) and also such a skin equivalent P obtained by carrying out this method.

Thus, the present invention relates first of all to a method for producing an unshrunken tissue equivalent T, in particular human unshrunken tissue equivalent T.

According to the invention, this method consists in producing a mixture m containing at least one element which is part of the composition of an extracellular matrix.

In one particular embodiment, such a mixture m is at least partly made up of such an extracellular matrix containing at least one such element.

With regard to said element which is part of the composition of an extracellular matrix, it may be made up of a biological constituent of such an extracellular matrix or of a synthetic substitute of such a biological constituent.

In one particular embodiment of the invention, such an element is made up of a biological constituent at least partly defined by at least one collagen.

In this respect, it will be observed that such a biological constituent can therefore be defined by a single collagen or by a plurality of collagens, more particularly of various types.

Another characteristic is that such a collagen preferably has an acid-soluble nature.

One additional characteristic is that such an element may be, in the mixture m, in the form of a dispersion of fibers or (and preferably) in the form of an extracellular matrix containing at least one such element.

According to the invention, the method consists in, after having produced the abovementioned mixture m, soaking at least one support S (FIG. 2a) having characteristics which make it possible to limit the geometric deformability, with at least one part of this mixture m.

Such a support S is at least partly made up of a pluridimensional structure, more particularly two-dimensional or (and preferably) three-dimensional (FIG. 1) structure.

This pluridimensional structure S comprises cavities which are in the form of interstices and/or alveoli, in particular of hexagonal shape.

In fact, and according to one preferred embodiment, such a support S is at least partly made up of a woven and/or knitted textile material, more particularly woven and/or knitted from fibers.

As can be seen in FIG. 1, such a textile material exhibits meshing, more particularly produced by weaving and/or knitting such fibers, and delimiting the abovementioned cavities (more particularly alveoli).

Such alveoli preferably have, as can be seen in FIG. 1, a hexagonal shape of which the six sides each have a length of about one millimeter, more particularly of about 1 mm±0.25 mm, preferably of about 1 mm±0.15 mm.

An additional characteristic is that such a textile material extends in at least one plane. In a first embodiment, corresponding to a two-dimensional structure, such a textile material comprises a single textile sheet which extends in a single plane. In a second embodiment, corresponding to a three-dimensional structure and illustrated in FIG. 1, such a textile material comprises at least two textile sheets:
  each extending in a plane parallel to the plane of another textile sheet;
  positioned at a predetermined distance from one another so as to define between them an interstice constituting a cavity;
  positioned such that the meshes, delimiting the alveoli of these two sheets, are out of line;
  connected to one another via filaments for preventing geometric deformation.

In such a textile material, the two textile sheets are positioned at a distance of about 2 mm±1 mm, preferably at a distance of about 2 mm±0.5 mm.

It will be observed that the use of such a textile material makes it possible to confer on the tissue equivalent (more particularly on the skin dermal equivalent) and also on the skin equivalent optimum properties in terms of bioadhesion, of thickness (with, more particularly, a skin dermal equivalent of which the thickness is 2 to 3 mm, whereas the prior art supports make it possible to obtain dermal equivalents of a few tens of millimeters only), of cell proliferation and of differentiation of fibroblasts into myofibroblasts.

Another characteristic of this support S is that it is preferably made of a biocompatible material, usually referred to as biomaterial.

According to another characteristic, the material of this support S may also be of nonresorbable type (more particularly made of polyester, polyamide—in particular nylon—or the like) or, and preferably, of resorbable type, more particularly of bioresorbable type.

In this respect, it will be observed that it is therefore more particularly the fibers of the textile material of this support S which are of biocompatible, or even resorbable, type.

An additional characteristic is that this support S is made of a material which has an elasticity and/or a rigidity (of about $0.050$ $N.mm^{-1}$ at 37° C. in aqueous medium) close to that of skin ($0.025$ $N.mm^{-1}$).

Yet another characteristic is that such a support S preferably adopts the form of a frame delimiting an opening which may be an emergent opening or a through-opening.

Additionally or alternatively, such an opening is preferably defined centrally relative to the support S.

Another characteristic of this support S is that it adopts a polygonal (square, rectangular, hexagonal) shape or, preferably, a round shape (FIG. 1).

Thus, and according to a first embodiment not represented, such a support S may adopt the shape of a plate comprising, firstly, such a frame delimiting an emergent opening, which is in particular central, and, secondly, a base from which this frame extends, more particularly while opening out.

However and according to one preferred embodiment of the invention illustrated in FIG. 1, such a support S adopts the shape of a ring, a torus or the like, comprising a frame delimiting a through-opening, which is in particular central.

In fact, and as will emerge from the remainder of the description, this support S will be placed in a container (more particularly a Petri dish or the like) which has a shape (usually round) for which the shape of this support S will preferably be suitable.

It is, more particularly, such a support S which is therefore soaked with at least one part of the mixture m (FIG. 2b), in particular by pouring at least one part of this mixture m onto this support S placed in a container (FIG. 2a).

According to the invention, this method also consists in producing, from the components of this mixture m, at least at the support S, a lattice L comprising at least one element which is part of the composition of an extracellular matrix.

In this respect, it will be observed that, in the mixture m containing at least one element which is part of the composition of an extracellular matrix (or even containing at least one such extracellular matrix), such an element (respectively such an extracellular matrix) is in the liquid state, which therefore makes it possible for such an element (respectively for such an extracellular matrix), when it is placed in the presence of said support S (in particular after having wetted the latter), to penetrate the structure of this support S so as to occupy at least one part (preferably all) of the internal volume of this support S and/or so as to be homogeneously distributed within this support S.

In such a case, it is more particularly the fibers of such an element (respectively of such an extracellular matrix) which will penetrate the support S and become entangled with the meshes of the structure of this support S.

Thus, by penetrating the structure of the support S, such an element (respectively such an extracellular matrix) will become organized so as to constitute, within this support S, a lattice L.

As mentioned above, the support S adopts the form of a frame with an opening. In this respect, it will be observed that, in addition to the penetration of an element (respectively of an extracellular matrix) into the structure of the support S, a part of at least one element (respectively of at least one extracellular matrix) contained in the mixture m will extend through such an opening and form, through this opening, a lattice L.

The method according to the invention also consists in attaching, to the structure of the support S, at least one part of the components of this mixture m, in particular at least one element that the lattice L comprises.

In this respect, it will be observed that, when at least one part of the components of the mixture m is attached to the structure of the support S, bioadhesion of at least one element, which is part of the composition of an extracellular matrix, and that the lattice L comprises, to this structure is in fact carried out.

Such a bioadhesion is, more particularly, carried out by polymerization of at least one such element of the lattice L which thus attaches to the meshes of the structure of the support S.

Advantageously, such a bioadhesion is facilitated by the use of a support S having the above-mentioned characteristics.

The method for producing an unshrunken tissue equivalent T thus consists in preventing the shrinking of at least the lattice L and in keeping at least this lattice L under tension on the support S.

In this respect, it will be observed that such keeping under tension results, firstly, from the attachment of this lattice L to the support S and, secondly, from the presence, within the lattice L, of contraction forces which would have a tendency to cause shrinking of the tissue equivalent T, but which, owing to the attachment of the lattice L to the support S, prevent this shrinking and enable the tissue equivalent T to remain isometric.

Advantageously, such keeping under tension makes it possible to optimize the organization of the lattice L, in particular relative to the support S.

An additional characteristic of the method of the invention consists in integrating fibroblasts into the lattice L.

According to a first embodiment, such fibroblasts can be incorporated into the lattice L by first of all producing a mixture m containing such fibroblasts, before producing such a lattice L from such a mixture m and in accordance with the abovementioned method.

However, and according to another embodiment, such fibroblasts are integrated by first of all producing the lattice L as mentioned above and from a mixture m free of fibroblasts, before migrating such fibroblasts into this lattice L.

In this respect, it will be observed that such fibroblasts may be of various origins.

In particular, such fibroblasts may be taken from a donor, more particularly the donor for whom the tissue equivalent T (more particularly the dermal equivalent D) obtained by means of the method in accordance with the invention is intended and in whom the tissue equivalent T (autologous graft) produced by means of this method will be grafted.

These fibroblasts can in particular be taken by biopsy of the skin of the donor.

Another characteristic of the method in accordance with the invention is that at least one cell culture of the fibroblasts is carried out, at least in the lattice L, in order to obtain the unshrunken tissue equivalent T.

In this respect, it will be observed that such a cell culture of the fibroblasts is carried out by immersing, in a culture medium C, at least one part (or even and preferably all) of the lattice L containing at least fibroblasts (FIG. 2c).

To do this and according to a first embodiment, the support S is immersed in such a culture medium C before attaching at least one part of the components of the abovementioned mixture m to the structure of this support S.

However and according to one preferred embodiment of the invention, this support S is immersed in such a culture medium C after having attached at least one part of the constituents of this mixture m to the structure of this support S.

With regard to this culture medium C, it is made up of a medium of DMEM type which may (or may not) contain a serum (more particularly a serum of the fetal calf serum type) and/or at least one antibiotic.

Another characteristic of the method is that the immersing of at least one part of the lattice L is carried out for a period of between 3 and 7 days, preferably about 5 days.

It should be observed that the cell culture of the fibroblasts is advantageously optimized by keeping the lattice L under tension on the structure of the support S and/or by using a support S having the above-mentioned characteristics.

In fact and in accordance with the method of the invention, when a cell culture of the fibroblasts is carried out, proliferation and/or differentiation of these fibroblasts is produced, in the culture medium C, at least within the lattice L (FIG. 2d) and in order to obtain the unshrunken tissue equivalent T.

Advantageously, the proliferation of the fibroblasts is accentuated by the use of a support S having the abovementioned characteristics.

With regard to the differentiation of the fibroblasts, said differentiation consists more particularly of maturation and/or cellular functionalization of fibroblasts to give myofibroblasts which express $\alpha$-sm actin and which have contractile properties.

Such a cell differentiation of the fibroblasts (more particularly a maturation/functionalization of these fibroblasts) is, advantageously and here again, optimized by keeping the lattice L under tension on the structure of the support S and/or by using a support S having the abovementioned characteristics.

Likewise, the use of such a support S makes it possible to notably increase the thickness of the tissue equivalent T produced by carrying out this method (about 2 to 3 mm), compared with the prior art techniques which make it possible to obtain a tissue equivalent T of which the thickness is notably less.

By carrying out the method described above, a tissue equivalent T (in particular a skin dermal equivalent D) is produced which advantageously has a structure comparable to and also properties (in particular in terms of mechanical, thickness, cell functionality, etc. characteristics) close to those of a natural tissue (in particular of natural skin dermis) in situ. Such a tissue equivalent T may thus be advantageously used as a skin model for tests for research purposes (in particular pharmacotoxicological tests), but also for therapeutic purposes.

Yet another characteristic of the invention is that the method makes it possible to produce an unshrunken tissue equivalent T in an autologous manner or, alternatively, an allogenic or xenogenic manner.

As mentioned above, the method in accordance with the present invention makes it possible to produce an unshrunken tissue equivalent T which is made up (by way of example and in a manner that is in no way limiting) of:
- a mucosal equivalent;
- a membrane equivalent, in particular amniotic membrane equivalent;
- a chorion equivalent;
- an integument equivalent, more particularly a skin dermal equivalent D, especially a human skin dermal equivalent D.

The present invention also relates to a method for producing a skin equivalent P, in particular a human skin equivalent P, comprising at least one dermal equivalent D and also at least one epidermal equivalent E.

According to the invention, this method consists in first of all producing an unshrunken tissue equivalent T made up of a skin dermal equivalent D, by carrying out the method for producing such a tissue equivalent T described above.

This method for producing a skin equivalent P then consists in producing, at the surface of the dermal equivalent D obtained (FIG. 3a), an epidermal equivalent E by developing or providing at least one layer K of keratinocytes, before carrying out at least one cell culture of these keratinocytes.

With regard to such keratinocytes, they can be obtained by any means, but are preferably taken (in particular by biopsy) from a donor, more particularly the donor for whom the skin equivalent P obtained by means of the method in accordance with the invention is intended and in whom this skin equivalent P (autologous graft) produced by means of this method will be grafted.

As mentioned above, the method consists in producing an epidermal equivalent E by developing at least one layer K of keratinocytes.

Thus and in accordance with the invention, when at least one layer K of keratinocytes is developed, the surface of the dermal equivalent D is seeded by depositing, on this surface, a suspension s containing keratinocytes (FIG. 3b) and at least one cell culture of the seeded keratinocytes is carried out.

In fact, the surface of the dermal equivalent D is seeded with between $10^5$ and $10^6$ keratinocytes per $cm^2$.

After having seeded the surface of the dermal equivalent D with keratinocytes, the method consists in carrying out a cell culture of the keratinocytes, in order to obtain at least one layer K of keratinocytes.

Such a cell culture can also be carried out after having provided the surface of the dermal equivalent D with at least one layer K of keratinocytes.

In this respect, it will be observed that such a cell culture is carried out by immersing (FIG. 3c), in a culture medium C' (which may or may not have substantially the same characteristics as the abovementioned culture medium C), at least the dermal equivalent D, or even also the keratinocytes seeded or provided at the surface of this dermal equivalent D.

In fact, such an immersion is carried out for a period of time that can range up to 7 days.

After a monolayer K of keratinocytes (in fact already constituting an epidermal equivalent E) has been obtained, the method for producing a skin equivalent P can be interrupted, in particular for use of such a skin equivalent P for research purposes (in particular pharmaceutical, pharmacological or toxicological research purposes).

However, and according to one preferred embodiment, this method can be continued such that, after development or provision of such a monolayer K of keratinocytes, cell differentiation of the keratinocytes of this layer K is induced, in order to obtain a pluristratified epidermal equivalent E.

In this respect, it should be observed that such a cell differentiation is induced by bringing, for a predetermined period of time, at least one part of the layer K of keratinocytes to emerge out of the culture medium C' and at the interface between this culture medium C' and a gas environment G.

In fact, and according to one preferred embodiment illustrated in FIG. 3d, such a cell differentiation is induced by bringing all of this layer K of keratinocytes to emerge out of the culture medium C' and at the interface between this culture medium C' and a gas environment G.

With regard to the period of time for which at least one part of the layer K of keratinocytes is brought to emerge, it may range up to 20 days.

With regard to the gas environment, it is at least partly made up of air (more particularly of ambient air), in particular supplemented with an additive.

In this respect, it will be observed that such an additive may thus be made of carbon dioxide.

By carrying out the method described above, a skin equivalent P is produced which advantageously has a structure comparable to and also properties (in particular in terms of mechanical, thickness, cell functionality, etc. characteristics) close to those of natural skin in situ.

This is essentially due to the fact that the dermal equivalent D (more particularly the lattice L that this dermal equivalent D comprises) obtained by carrying out the method in accordance with the invention is much better organized than a dermal equivalent D produced by carrying out a prior art method.

In fact, this better organization results essentially from keeping said lattice L under tension on the support S, thus preventing natural shrinking thereof.

The skin equivalent P (more particularly an epidermized dermal equivalent D) obtained by carrying out this method may advantageously be used for research purposes, in particular pharmaceutical and/or pharmacological research purposes, in particular as a skin model for pharmacological and/or toxicological tests.

However, this skin equivalent P may also be used for therapeutic purposes, in particular as a graft in the context of grafting (in particular of autologous type) of such a skin equivalent P.

Thus, and as mentioned above, the invention relates to a method for producing an unshrunken tissue equivalent T (in particular a skin dermal equivalent D) and also a method for producing a skin equivalent P.

The present invention thus also relates to an unshrunken tissue equivalent T (in particular human unshrunken tissue equivalent T), more particularly (but not exclusively) obtained by carrying out the method described above.

As mentioned above, such an unshrunken tissue equivalent T can thus, and by way of nonlimiting example, be made up of:
- a mucosal equivalent;
- a membrane equivalent, in particular amniotic membrane equivalent;
- a chorion equivalent;
- an integument equivalent, more particularly a skin dermal equivalent D, especially human skin dermal equivalent D.

Such a tissue equivalent T thus comprises:
- a support S (more particularly having the characteristics described above) which is at least partly made up of a pluridimensional structure comprising cavities;
- a lattice L which firstly comprises at least one element (more particularly having the characteristics described above) which is part of the composition of an extracellular matrix, which secondly is attached to (more particularly as described above, in particular by bioadhesion) and kept under tension on this support S, and which thirdly integrates at least fibroblasts and/or myofibroblasts resulting from cell differentiation of such fibroblasts.

This invention also relates to a skin equivalent P (in particular human skin equivalent P) comprising firstly at least one dermal equivalent D and secondly at least one epidermal equivalent E.

In fact, such a skin equivalent P may in particular (but not exclusively) be (at least partly) obtained by carrying out the method described above.

In particular, at least the dermal equivalent D of this skin equivalent P may be obtained by carrying out the corresponding method described above and/or have the characteristics described above.

This skin dermal equivalent D may thus preferably be made up of an unshrunken tissue equivalent T having the characteristics described above and/or be obtained by carrying out the corresponding method described above.

Furthermore, this skin equivalent P has the characteristics described above.

In particular, this skin equivalent P comprises a dermal equivalent D and also an epidermal equivalent E, each having the characteristics described above.

Thus, the epidermal equivalent E comprises at least one layer K of keratinocytes.

However, and according to another characteristic of this skin equivalent P, the epidermal equivalent E in fact comprises a plurality of superimposed strata of keratinocytes in order to obtain a pluristratified epidermal equivalent.

In this respect, it will be observed that each stratum contains keratinocytes exhibiting a differentiation state different than that of another stratum.

Finally, the invention also relates to a support S having the characteristics mentioned above and also to the use of such a support S for producing, as appropriate, a dermal equivalent D or a skin equivalent P (in particular human skin equivalent P).

The invention claimed is:

1. An unshrunken human skin equivalent, comprising at least one skin dermal equivalent and at least one epidermal equivalent,
   wherein the skin dermal equivalent comprises
   (a) a biocompatible support, characterized as:
      having a pluridimensional structure comprising cavities in the form of interstices and/or alveoli,
      comprising at least two mesh textile sheets, said mesh defining cavities in each textile sheet,
      wherein each of said at least two textile sheets extend in a plane parallel to the plane of another textile sheet,
      wherein each of said at least two textile sheets are positioned at a predetermined distance from one another so as to define a space between the at least two textile sheets,
      wherein each of said at least two textile sheets are positioned such that the meshes defining the cavities of each textile sheets are out of line; and
      wherein the at least two textile sheets are connected to one another via filaments for preventing geometric deformation; and
   (b) a lattice, wherein said lattice is characterized as:
      comprising at least one extracellular matrix component,
      being attached by bioadhesion to the (a) support and is kept under tension on said support, and
      further comprises at least fibroblasts and/or myofibroblasts resulting from cell differentiation of such fibroblasts; and
   wherein the epidermal equivalent includes at least one layer of keratinocytes.

2. The unshrunken human skin equivalent of claim 1,
   wherein the (a) biocompatible support forms a polygonal or round shaped frame which defines at least one central opening; and
   wherein the (b) lattice is adhered to the frame and also extends over the at least one central opening,
   adopting a polygonal or round shape;
   at least one element which is part of the composition of an extracellular matrix penetrates the structure of the support, extends through the opening of the frame, and forms a lattice, this being within this structure and through this opening.

3. The unshrunken human skin equivalent of claim 1,
   wherein the at least two mesh textile sheets are produced by weaving and/or knitting of fibers.

4. The unshrunken human skin equivalent of claim 1, wherein the (a) biocompatible support is made of a bioresorbable material.

5. The unshrunken human skin equivalent of claim 1, wherein the bioadhesion which attaches the (b) lattice to the (a) support is due to polymerization of the at least one extracellular matrix component.

6. The unshrunken human skin equivalent of claim 1, wherein the extracellular matrix component is an acid soluble collagen.

7. The unshrunken human skin equivalent of claim 1, wherein the epidermal equivalent comprises a plurality of superimposed strata of keratinocytes, each stratum of said plurality of superimposed strata containing keratinocytes exhibiting a different phenotype than keratinocytes of another stratum of said plurality of superimposed strata.

* * * * *